United States Patent [19]
Grögler et al.

[11] 4,360,603
[45] Nov. 23, 1982

[54] PROCESS FOR THE PREPARATION OF COMPOUNDS CONTAINING S-TRIAZINE UNITS AND ISOCYANATE GROUPS OR ISOCYANATE-REACTIVE GROUPS AND THE PRODUCTION OF POLYURETHANES CONTAINING THESE FILLERS

[75] Inventors: Gerhard Grögler, Leverkusen; Werner Rasshofer; Richard Kopp, both of Cologne, all of Fed. Rep. of Germany

[73] Assignee: Bayer Aktiengesellschaft, Leverkusen, Fed. Rep. of Germany

[21] Appl. No.: 323,331

[22] Filed: Nov. 20, 1981

[30] Foreign Application Priority Data

Dec. 2, 1980 [DE] Fed. Rep. of Germany ....... 3045470

[51] Int. Cl.³ .............................................. C08G 18/14
[52] U.S. Cl. .................................... 521/159; 521/161; 528/59; 528/60; 528/61; 528/64; 528/65; 528/66; 544/197

[58] Field of Search .................. 521/159, 161; 528/59, 528/60, 61, 64, 65, 66; 544/197

[56] References Cited

U.S. PATENT DOCUMENTS 4,255,570  3/1981  Grögler et al. ..................... 544/197

*Primary Examiner*—Maurice J. Welsh
*Attorney, Agent, or Firm*—Gene Harsh; Joseph C. Gil; Richard A. Elder

[57] ABSTRACT

This invention relates to a process for the preparation of compounds which contain s-triazine units and isocyanate groups or isocyanate-reactive groups and which melt without decomposition, by the reaction of triisocyanates containing s-triazine units with compounds containing isocyanate-reactive groups, and the use of these products as fillers which can be chemically fixed in the production of polyurethanes by the isocyanate polyaddition process.

5 Claims, No Drawings

PROCESS FOR THE PREPARATION OF COMPOUNDS CONTAINING S-TRIAZINE UNITS AND ISOCYANATE GROUPS OR ISOCYANATE-REACTIVE GROUPS AND THE PRODUCTION OF POLYURETHANES CONTAINING THESE FILLERS

BACKGROUND OF THE INVENTION

Polyisocyanates containing s-triazine units prepared by the reaction of melamine with excess quantities of aromatic diisocyanates containing isocyanate groups with differing reactivities are described in European Pat. No. 893 (corresponding to U.S. patent application Ser. No. 930,611, filed Aug. 3, 1978 and now U.S. Pat. No. 4,255,570, issued Mar. 10, 1981). The compounds described in that prior publication are solid substances which range in their solubility in organic media from difficult to solubilize to insoluble and which are very high melting and decompose in the melt. Due to their high melting point and their poor solubility or compatibility, the usefulness of the abovementioned polyisocyanates as reactive fillers in the production of polyurethanes by the isocyanate polyaddition process is strictly limited.

It was therefore an object of the present invention, starting from the known polyisocyanates containing s-triazine units, to develop fillers capable of being chemically fixed which do not have those disadvantages, but rather are capable of melting without decomposition and/or have improved compatibility with the starting materials used for the production of polyurethanes.

SUMMARY OF THE INVENTION

This invention thus relates to a process for the preparation of compounds containing s-triazine units and isocyanate groups or isocyanate-reactive groups which can melt without decomposition and are suitable as chemically-fixed fillers for polyurethanes, characterized in that triisocyanates corresponding to the formula

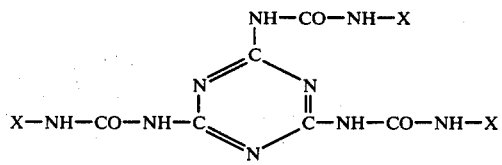

wherein
X denotes a group obtained by removal of the more highly reactive isocyanate group from an aromatic diisocyanate in which the isocyanate groups differ in their reactivity in isocyanate addition reactions,
are reacted with at least difunctional compounds containing isocyanate reactive groups, using an equivalent ratio of isocyanate groups to isocyanate-reactive groups of at least 1.5:1 or an equivalent ratio of isocyanate-reactive groups to isocyanate groups of at least 1.5:1.

This invention also relates to the use of the products obtained according to the invention as fillers which can be chemically fixed in the production of polyurethanes by the isocyanate polyaddition process.

DETAILED DESCRIPTION OF THE INVENTION

In the process according to the invention, polyisocyanates of the above-mentioned formla containing s-triazine units in which X has the meaning indicated above are used. It is advantageous to use those polyisocyanates of the above formula in which X denotes a 3-isocyanato-4-methylphenyl group or a 4-(2-isocyanatobenzyl)-phenyl group. The preparation of such polyisocyanates has been described, for example, in European Patent Specification No. 893 (U.S. patent application Ser. No. 930,611, now U.S. Pat. No. 4,255,570, issued Mar. 10, 1981).

Suitable polyisocyanates with s-triazine units for the process according to the invention are, in particular, N,N',N''-tris-(3-isocyanato-4-methyl-phenyl-amino-carbonyl)-melamine or N,N',N''-tris-[4-(2-isocyanatobenzyl)-phenyl-amino-carbonyl]-melamine, although any other aromatic polyisocyanates containing s-triazine units conforming to the above definition may also be used for the process according to the invention.

The reactants for the above-mentioned polyisocyanates containing s-triazine units include any compounds having a molecular weight of from 32 to 10,000, preferably from 60 to 6,000, in particular from 60 to 300, which contain isocyanate-reactive groups and are at least difunctional in the isocyanate addition reaction.

Suitable reactants for the polyisocyanates containing s-triazine units are in particular:

(a) Compounds within the above molecular weight ranges which have at least two alcoholic hydroxyl groups and do not contain primary or secondary amino groups, e.g., simple alkane polyols such as ethylene glycol; 1,2- or 1,3-dihydroxy propane; 1,4-, 1,3- or 2,3-dihydroxybutane; 1,6-dihydroxy hexane; 1,8-dihydroxyoctane; neopentyl glycol; 1,4-bis-hydroxymethylcyclohexane; glycerol; trimethylol propane; hexanetriol-(1,2,6); pentaerythritol; sorbitol; low molecular weight polyols containing ether groups; such as diethylene glycol, dipropylene glycol, triethylene glycol, or tripropylene glycol; and the corresponding polyalkylene glycols with a molecular weight of up to 300. Also the higher molecular weight polyols with ether or ester groups known in polyurethane chemistry, e.g., the known ethoxylation and/or propoxylation products of the above-mentioned low molecular weight polyols or other starter molecules such as water or amines containing at least two NH bonds or the reaction products of at least two basic carboxylic acids or of their anhydrides with low molecular weight polyols of the type exemplified above; the acid component in the polyester polyols being, for example, adipic acid, phthalic acid, phthalic acid anhydride, hexahydrophthalic acid, hexahydrophthalic acid anhydride, maleic acid, maleic acid anhydride, dimerized or trimerized unsaturated fatty acids or terephthalic acid. Castor oil may also be used as polyol component.

(b) Hydroxy alkylamines, i.e., compounds which in addition to at least one hydroxyl group have at least one primary or secondary amino group, e.g., ethanolamine, diethanolamine, isopropanolamine, diisopropanolamine, N-hydroxyethyl-ethylene diamine or N-hydroxyethylhexylene diamine.

(c) Polyamines in the above-mentioned molecular weight ranges containing at least two primary and/or secondary amino groups, e.g., hydrazine; ethylenediamine; 1,6-diaminohexane; 2,4- and/or 2,6-diaminotoluene; 2,4'- or 4,4'-diaminodiphenyl methane; 2,4- or 2,6-hexahydrotoluene diamine; perhydrogenated 2,4'- or 4,4'-diaminodiphenyl methane; p-xylylene diamine; cycloaliphatic triamines, for example those according to German Offenlegungsschrift No. 2,614,244; bisanthranilic acid esters according to German Offenlegungsschriften 2,040,644 or 2,160,590; 3,5- and 2,4-diaminobenzoic acid esters, for example according to German Offenlegungsschrift No. 2,025,900; diamines containing ester groups according to German Offenlegungsschriften 1,803,635 (U.S. Pat. No. 3,681,290 or 3,736,350) 2,040,650 and 2,160,589; diamines with ether groups according to German Offenlegungsschrift No. 1,770,525 or German Offenlegungsschrift No. 1,809,172 (U.S. Pat. No. 3,654,364 or 3,736,295); aromatic diamines substituted with alkylthio groups according to German Offenlegungsschrift No. 2,638,760; or amino alkylthio anilines according to German Offenlegungschrift No. 2,374,574.

Any mixtures of the compounds exemplified above may, of course, be used in the process according to the invention. Any other compounds containing isocyanate-reactive groups may also be used in the process according to the invention, provided they have at least two isocyanate-reactive groups and are within the molecular weight range of from 32 to 10,000. In addition to the preferred starting materials exemplified under (a) through (c) above, there may also be used in the process according to the invention the polythioethers, polyacetals, polycarbonates, polyester amides, polyamides, polyhydroxyl compounds containing urethane or urea groups and polycarboxylic acids used in polyurethane chemistry, for example those of the type exemplified above for the production of polyester polyols. Modification products of the polyhydroxyl compounds exemplified under (a) may also be used, for example, dispersions of polyaddition products, polycondensation products or polymers in the polyether polyols exemplified above.

When carrying out the process according to the invention, the isocyanate groups and isocyanate-reactive groups are used in a suitable equivalent ratio to each other to ensure that no polyurethanes, i.e., high molecular weight compounds, but only comparatively low molecular weight compounds containing isocyanate groups or isocyanate-reactive groups will be formed. This means that in the process according to the invention, the reactants are used in an equivalent ratio (i) of isocyanate groups to isocyanate-reactive groups of at least 1.5:1, preferably in the range of from 2n:1 to 4n:1 or (ii) of isocyanate-reactive groups to isocyanate groups of at least 1.5:1, preferably in the range of from 0.8n:1 to 1.2n:1, where n is the functionality of the reactants having isocyanate-reactive groups. The nature and quantitative proportions of the reactants are otherwise chosen so that the end products of the process have a maximum molecular weight of about 30,000, preferably 10,000, most preferably 2,000. The molecular weight of the starting materials and of the end products may be calculated from the functionality and the functional group content.

The process according to the invention may, for example, be carried out as follows: a mixture of a polyisocyanate of the type mentioned above and at least one compound with isocyanate-reactive groups of the type mentioned above are reacted together with stirring for a period of from 0.25 to 25 hours, preferably from 0.5 to 15 hours. If the reactants for the polyisocyanates containing s-triazine units contain primary or secondary amino groups, the process according to the invention is generally carried out at temperatures in the range of from 0° to 100° C., preferably from 20° to 80° C., whereas if the reactants contain hydroxyl groups, the process is carried out in the temperature range of from 40° to 190° C., preferably from 60° to 160° C. The reaction may be carried out solvent-free or in a solvent which is inert towards isocyanate groups, e.g., dioxane, tetrahydrofuran, benzene, toluene, chlorobenzene, dichlorobenzene, nitrobenzene, xylene or chlorinated aliphatic hydrocarbons.

The reaction according to the invention could in principle also be carried out in the presence of a liquid reaction medium containing isocyanate-reactive groups, provided the isocyanate-reactive starting materials are more highly isocyanate-reactive than the isocyanate-reactive groups of the reaction medium. Thus for example, a polyester polyol or polyether polyol with a molecular weight in the range of from 1,000 to 10,000, preferably from 1,000 to 4,000, may be used as reaction medium, and the reaction according to the invention may be carried out between the polyisocyanates containing s-triazine units and starting materials of the type exemplified which contain primary or secondary amino groups. If relatively high molecular weight polyether polyols or polyester polyols are used, dispersions or solutions of the end products according to the invention are then obtained in situ in those polyhydroxyl compounds. The same result may also be obtained by exclusively using excess quantities of relatively high molecular weight compounds of the type mentioned above, which may serve both as reactants and as reaction medium. If the starting materials used contain primary or secondary amino groups, much less reactive low molecular weight alcohols, for example ethanol, may be used as reaction medium, since the addition reaction takes place selectively between the amino groups and the isocyanate groups.

The known accelerators for the isocyanate addition reaction are often used in the process according to the invention. These include, for example, amidines such as diazabicyclo undecene, N-methyl-2-methyl-tetrahydropyrimidine, tertiary amines such as triethylene diamine and metal catalysts such as tin-(II) octoate, dibutyl tin laurate or lead dioctoate.

The end products obtained from the process according to the invention are compounds which generally contain approximately 0.1 to 12% by weight, preferably 4 to 10% by weight of s-triazine units (molecular weight=78) and from 1.25 to 900, preferably from 100 to 700 millimol per 100 g of isocyanate groups or isocyanate-reactive groups.

The fillers obtained from the process according to the invention cover a wide range of melting points according to the nature and quantitative proportions of the starting materials used. The end products of this process differ from the starting polyisocyanates containing s-triazine units, however, by having a lower melting point and/or improved compatibility with the starting materials of polyurethane chemistry. They are suitable in particular as fillers which may be chemically fixed in the production of polyurethanes by the isocyanate polyaddition process. The compounds are chemically fixed in either the polyisocyanate component or the component with isocyanate-reactive groups, depending on whether the compounds used contain isocyanate groups or isocyanate-reactive groups. Due to their lower melting point, the end products of the process according to the invention are also far better suited as binder components for two component polyurethane powder lacquers than are the polyisocyanates with s-triazine units according to European Patent No. 893 on which they are based.

The polyurethanes produced using the products of the process according to the invention are distinguished in particular by their improved mechanical properties and improved fire characteristics.

The invention is further illustrated, but is not intended to be limited by the following examples in which all parts and percentages are by weight unless otherwise specified.

EXAMPLE 1

100 g of N,N',N''-tris-(3-isocyanato-4-methyl-phenyl-amino-carbonyl)-melamine (0.154 mol) are suspended in 200 ml of ethanol at room temperature, and 28.3 g of ethanolamine (0.471 mol) are added. The reaction mixture is then stirred for 2 hours at 60° C. The solid product is removed by suction filtration and washed with 100 ml of ethanol.

The reaction product obtained melts at 224° to 226° C. and contains 9.4% of triazine units and 6.5% of hydroxyl units.

EXAMPLE 2

100 g of the triisocyanate from Example 1 (0.154 mol) are suspended in 200 ml of ethanol at room temperature. 48 g of N-hydroxyethyl-ethylene diamine (0.463 mol) are then added with stirring over a period of 20 minutes at room temperature. Stirring is then continued for 1 more hour and the resulting solid product is suction filtered and washed with ether.

130 g of a substance melting at 216° to 219° C. and containing 8.1% of triazine units and a total of 10% of aminic amino groups and hydroxyl groups is obtained.

EXAMPLE 3

100 g (0.154 mol) of the triisocyanate from Example 1 are suspended in 200 ml of ethanol, and 54.6 g of N-hydroxyethyl-propylene diamine-(1,3) (0.463 mol) are added over a period of 30 minutes with stirring. Stirring is then continued for 90 minutes at 62° C. The resulting solid product is suction filtered and washed first with 50 ml of acetone and then with 50 ml of ethanol.

142 g of a substance melting at 222° to 223° C. and containing 7.8% of triazine units and a total of 9.6% of hydroxyl groups and aminic amino groups is obtained.

EXAMPLE 4

64.8 g of the triisocyanate from Example 1 (0.1 mol) and 100 g of triethylene glycol (0.67 mol) are stirred for 90 minutes at 140° C. The reaction mixture is then taken up in acetone and the reaction product is suction filtered. The product is washed with 50 ml of acetone and then with 50 ml of ether.

The substance obtained melts at 280° to 300° C. and contains 7.1% of triazine units and 4.6% of hydroxyl groups.

EXAMPLE 5

50 g of the triisocyanate from Example 1 (0.077 mol) are suspended in 100 ml of toluene. 2.31 g of ethylene diamine (0.0385 mol) are then added at room temperature. The mixture is stirred for 2 hours at 60° C.

52 g of a substance melting at 288° to 291° C. is obtained after suction filtration and washing with toluene. The substance contains 11.5% of triazine units and 12.4% of isocyanate groups.

EXAMPLE 6

1,000 g of a polypropylwene glycol having a molecular weight of 1,000 (1 mol) are stirred for 15 hours together with 63 g (0.97 mol) of the triisocyanate from Example 1 in the presence of 0.5 g of dibutyl tin dilaurate at 140° to 150° C.

A solution of a reaction product of polypropylene glycol with the triisocyanate in excess polypropylene glycol is obtained. The solution has a hydroxyl group content of 2.8%.

EXAMPLE 7

40 g of diethanolamine (0.38 mol) are dissolved in 100 ml of dioxane. 83.0 g (0.128 mol) of the triisocyanate from Example 1 are added portion-wise with stirring at 50° C. over a period of 5 minutes. Stirring is continued for 30 minutes at 50° C. The resulting solid product is suction filtered and washed with ether.

120 g of a substance melting at 223° C. and containing 8.1% of triazine units and 10.6% of hydroxyl groups is obtained.

EXAMPLES 8 TO 12

In these examples, the triisocyanate from Example 1 is reacted with various amino alcohols or diamino alkanes in a polyether A of OH number 42 prepared by the propoxylation of a mixture of trimethylol propane and propylene glycol (molar ratio=3:1) followed by ethoxylation of the propoxylation product using a molar ethylene oxide/propylene oxide ratio of 3:7. The aminic reactants are in each case dissolved in polyether and the quantities of triisocyanate indicated in Table 1 are added. The reaction is carried out for 30 minutes at 50° C. with stirring. To determine the melting point, a small portion of the solid substance which is in all cases obtained as a dispersion in the polyether is isolated by filtration and washed with diethyl ether.

TABLE 1

| | (Quantities in g): | | | | |
|---|---|---|---|---|---|
| | Example 8 | Example 9 | Example 10 | Example 11 | Example 12 |
| Polyether A | 500 | 500 | 500 | 500 | 500 |
| Diethanolamine | 20 | — | — | — | — |
| Diisopropanolamine | — | 25.3 | 50.6 | 17.3 | 11.9 |
| Ethylenediamine | — | — | — | 1.8 | 3 |
| Triisocyanate | 41.8 | 41.8 | 83.6 | 41.8 | 41.8 |
| Solid content % | 11 | 11.8 | 21.2 | 10.9 | 10.2 |
| Melting point of solid | 226 | 350 | 340–350 | 340 | 340 |

EXAMPLES 13 TO 18

These examples illustrate the use of the suspensions prepared in Examples 8 to 12 for the production of rigid polyurethane integral foams (Examples 13 to 17). Example 18 is a comparison example in which the products of the process according to the invention are not used. The results are summarized in Table 2 below.

TABLE 2

| | Example 13 | Example 14 | Example 15 | Example 16 | Example 17 | Example 18 |
|---|---|---|---|---|---|---|
| Suspension from Example 8 | 40 | — | — | — | — | — |

TABLE 2-continued

|  | Example 13 | Example 14 | Example 15 | Example 16 | Example 17 | Example 18 |
|---|---|---|---|---|---|---|
| Suspension from Example 9 | — | 40 | — | — | — | — |
| Suspension from Example 10 | — | — | 40 | — | — | — |
| Suspension from Example 11 | — | — | — | 40 | — | — |
| Suspension from Example 12 | — | — | — | — | 40 | — |
| Polyether B[1] | 60 | 60 | 60 | 60 | 60 | 60 |
| Polyether A | — | — | — | — | — | 40 |
| OS 50[2] | 1 | 1 | 1 | 1 | 1 | 1 |
| E[3] | 3 | 3 | 3 | 3 | 3 | 3 |
| K[4] | 3 | 3 | 3 | 3 | 3 | 3 |
| TMG[5] | 0.5 | 0.5 | 0.5 | 0.5 | 0.5 | 0.5 |
| H$_3$PO$_4$ (85%) | 0.2 | 0.2 | 0.2 | 0.2 | 0.2 | 0.2 |
| Trichlorofluoromethane | 10 | 10 | 10 | 10 | 10 | 10 |
| Component B[6] | 146.5 | 146.5 | 149.2 | 145.3 | 144.5 | 143 |

[1] Polyether B = polyether with OH number 860 obtained by the chemical addition of propylene oxide to trimethylol propane.
[2] OS 50 = stabilizer of Goldschmidt, Essen based on a polysiloxane-polyalkylene oxide block copolymer.
[3] E = reaction product of 1 mol of 3-dimethyl amino propylamine -(1) with 2 moles of oleic acid (emulsifier).
[4] K = dimethyl benzyl amine as catalyst.
[5] TMG = Tetramethyl guanidine.
[6] Polyisocyanate obtained by the phosgenation of aniline-formaldehyde condensates and having a viscosity of 130 mPas at 25° C. and an isocyanate content of 31% by weight.

The compounds first mentioned in Table 2 are in each case mixed with component A and then stirred for about 30 seconds with a high speed stirrer to charge them with air. The given quantity of component B is then added and the mixture is vigorously mixed for about 10 to 15 seconds and introduced into an open paper mold (measuring 250×120×120 mm). Foaming begins and the start time (time from the beginning of mixing of components A and B to the onset of foaming) and thread drawing time (time from beginning of mixing components A and B to the time when a wooden rod (diameter about 2 mm) dipped into the rising foam at intervals of a second is found to draw threads from the foam when removed) are determined.

To produce a test plate, the mixture of components A and B is poured immediately after stirring into an upright aluminum molding tool thermostatically controlled at about 60° C. and a plate measuring 200×200×10 mm³ is formed. After a dwell time of 10 minutes, the plate is removed from the mold and left for 2 days at room temperature and normal atmospheric moisture. The surface hardness is then measured and a piece of the test plate measuring 200×100×10 mm³ is subjected to a heat endurance test in which the plate is placed with its 100 mm edge on a U-shaped wooden frame (contact at the edges over about 5 mm) and at its center, the plate is loaded with a 1 kg weight at 110° C. for 1 hour. After the test, the sagging of the plate in the middle is determined in mm and standardized according to the formula: Sagging$_{(RG)}$×(RG/600), to the unit weight (RG) 600.

The following data were obtained:

|  | Example 13 | Example 14 | Example 15 | Example 16 | Example 17 | Example 18 |
|---|---|---|---|---|---|---|
| Start time (sec) | 24 | 22 | 22 | 20 | 21 | 24 |
| Thread Drawing Time (sec) | 38 | 33 | 35 | 31 | 32 | 40 |
| Test plate |  |  |  |  |  |  |
| Unit weight | 510 | 530 | 550 | 510 | 580 | 580 |
| Shore D | 64 | 66 | 67 | 64 | 69 | 71 |
| Sagging (mm) | 2.5 | 1.5 | 1.0 | 3.0 | 2.1 | 3.5 |
| Standardized to 600 | 2.125 | 1.325 | 0.917 | 2.55 | 2.03 | 3.38 |

What is claimed is:

1. A process for the preparation of compounds containing s-triazine units and isocyanate groups or isocyanate-reactive groups, which compounds are capable of melting without decomposition and are suitable for use as fillers which can be chemically fixed in polyurethanes, characterized in that triisocyanates corresponding to the formula

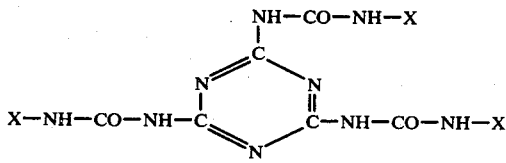

wherein

X denotes a group obtained by removal of the more highly reactive isocyanate group from an aromatic diisocyanate having isocyanate groups differing in their reactivity in the isocyanate addition reaction, are reacted with at least difunctional compounds containing isocyanate-reactive groups, using an equivalent ratio of isocyanate groups to isocyanate-reactive groups of at least 1.5:1 or an equivalent ratio of isocyanate-reactive groups to isocyanate groups of at least 1.5:1.

2. A process according to claim 1, characterized in that the compounds containing isocyanate-reactive groups are compounds having a maximum molecular weight of 10,000 selected from the group consisting of
   (a) polyhydroxyl compounds which have no primary or secondary amino groups,
   (b) hydroxy alkylamines having primary and/or secondary amino groups and
   (c) polyamines having at least 2 primary and/or secondary amino groups.

3. A process according to claims 1 or 2, characterized in that
   X denotes a 3-isocyanato-4-methyl-phenyl group or a 4-(2-isocyanatobenzyl)-phenyl group.

4. A process according to claims 1 or 2, characterized in that the compounds which are at least difunctional and have isocyanate-reactive groups have a maximum molecular weight of 300.

5. A process for the production of polyurethane comprising reacting an organic polyisocyanate with one or more active hydrogen-containing materials in the presence of filler materials, the improvement wherein said filler material comprise compounds containing s-triazine units and isocyanate groups or isocyanate-reactive groups which are capable of melting without decomposition and which can be chemically fixed in the polyurethane are obtained by reacting triisocyanates corresponding to the formula

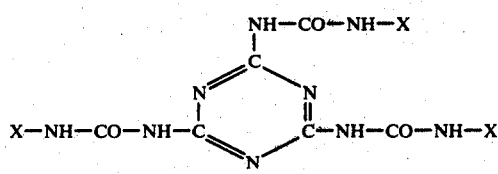

wherein
X denotes a group obtained by removal of the more highly reactive isocyanate group from an aromatic diisocyanate having isocyanate groups differing in their reactivity in the isocyanate addition reaction with at least difunctional compounds containing isocyanate-reactive groups, using an equivalent ratio of isocyanate groups to isocyanate-reactive groups of at least 1.5:1 or an equivalent ratio of isocyanate-reactive groups to isocyanate groups of at least 1.5:1.

* * * * *